United States Patent
Xia et al.

(10) Patent No.: US 11,833,078 B2
(45) Date of Patent: Dec. 5, 2023

(54) MULTI-SPOT OPHTHALMIC LASER

(71) Applicant: Ellex Medical Pty Ltd, Mawson Lakes (AU)

(72) Inventors: Wei Xia, Mawson Lakes (AU); Victor Previn, Mawson Lakes (AU); Robin McWilliams, Mawson Lakes (AU); John Marshall, Mawson Lakes (AU)

(73) Assignee: ELLEX MEDICAL PTY LTD, Mawson Lakes (AU)

( * ) Notice: Subject to any disclaimer, the term of this patent is extended or adjusted under 35 U.S.C. 154(b) by 0 days.

(21) Appl. No.: 16/638,745

(22) PCT Filed: Aug. 17, 2018

(86) PCT No.: PCT/AU2018/050879
§ 371 (c)(1),
(2) Date: Feb. 12, 2020

(87) PCT Pub. No.: WO2019/033176
PCT Pub. Date: Feb. 21, 2019

(65) Prior Publication Data
US 2021/0128348 A1    May 6, 2021

(30) Foreign Application Priority Data
Aug. 18, 2017    (AU) ................. 2017903330

(51) Int. Cl.
*A61F 9/008* (2006.01)
*G02B 6/04* (2006.01)
(Continued)

(52) U.S. Cl.
CPC ........... *A61F 9/008* (2013.01); *G02B 6/04* (2013.01); *G02B 19/0009* (2013.01);
(Continued)

(58) Field of Classification Search
CPC ............ A61F 9/008; A61F 2009/00863; A61F 2009/00872; A61F 9/00821;
(Continued)

(56) References Cited

U.S. PATENT DOCUMENTS 4,884,884 A * 12/1989 Reis ................. A61F 9/008
351/221
6,066,128 A * 5/2000 Bahmanyar ........... A61F 9/008
606/4
(Continued)

FOREIGN PATENT DOCUMENTS

JP    2006-521930 A    9/2006
JP    2007-159740 A    6/2007
(Continued)

OTHER PUBLICATIONS

EP Application No. 18846727.8, Extended European Search Report dated Mar. 29, 2021.
(Continued)

*Primary Examiner* — Joseph M Dietrich
*Assistant Examiner* — Michael T. Holtzclaw
(74) *Attorney, Agent, or Firm* — Alston & Bird LLP

(57) ABSTRACT

A multi-spot ophthalmic laser device that produces spatially distributed laser spots with the spatial distribution of the laser spots defined by a spot diameter to space ratio in the range 1:2 to 1:20. The multi-spot ophthalmic laser device comprises: a laser module producing a laser pulse or sequence of laser pulses each having: a pulse duration in the range of 10 ps to 20 μs; a wavelength in the range 500 nm to 900 nm; and a pulse energy in the range 10 μJ to 10 mJ per pulse; and an optical beam profiling module that modifies an output beam profile of each pulse of the laser module to deliver multiple spatially distributed laser spots of defined size and energy. The multi-spot ophthalmic laser device is
(Continued)

used in a method of improving the function of the retina of a human eye by irradiation through the cornea of the eye to the retinal pigmented epithelium by a treatment laser having a beam profile with spatially distributed energy peaks.

7 Claims, 6 Drawing Sheets

(51) Int. Cl.
  *G02B 19/00* (2006.01)
  *G02B 27/09* (2006.01)
(52) U.S. Cl.
  CPC ..... *G02B 19/0047* (2013.01); *G02B 27/0944* (2013.01); *A61F 2009/00863* (2013.01); *A61F 2009/00872* (2013.01)
(58) Field of Classification Search
  CPC .............. A61F 9/00823; A61F 9/00814; A61F 9/00817; G02B 6/04; G02B 19/0009; G02B 19/0047; G02B 27/0944; A61B 2018/00321; A61B 2018/00589; A61B 2018/2211; A61B 2018/2266; A61B 2018/2294; A61B 18/20; A61B 18/203; A61B 2018/00779
  See application file for complete search history.

(56) References Cited

U.S. PATENT DOCUMENTS

| | | | |
|---|---|---|---|
| 6,096,028 A | | 8/2000 | Bahmanyar et al. |
| 9,381,116 B2 | | 7/2016 | Luttrull et al. |
| 2008/0051770 A1* | 2/2008 | Scheller | ................. A61F 9/008 606/4 |
| 2010/0152716 A1* | 6/2010 | Previn | ..................... A61F 9/008 606/4 |
| 2011/0172649 A1 | 7/2011 | Schuel et al. | |
| 2012/0150159 A1* | 6/2012 | Kunath-Fandrei | ...... A61F 9/008 606/4 |
| 2016/0082294 A1 | 3/2016 | Luttrull et al. | |
| 2016/0346126 A1* | 12/2016 | Luttrull | ................ A61F 9/00821 |
| 2016/0354242 A1* | 12/2016 | Palanker | ................ A61F 2/1602 |
| 2018/0243137 A1* | 8/2018 | Diao | ....................... A61B 18/22 |

FOREIGN PATENT DOCUMENTS

| | | |
|---|---|---|
| JP | 2008-510529 A | 4/2008 |
| JP | 2010-158331 A | 7/2010 |
| JP | 2011-230159 A | 11/2011 |
| JP | 2012-148071 A | 8/2012 |
| JP | 2013-500769 A | 1/2013 |
| JP | 2015-100583 A | 6/2015 |
| KR | 2005-0111790 A | 11/2005 |
| KR | 2013-0058011 A | 6/2013 |
| WO | WO 2004/003468 A | 1/2004 |
| WO | WO 2008/024848 A2 | 2/2008 |
| WO | WO 2009/009246 A1 | 1/2009 |
| WO | WO 2019/033176 A1 | 2/2019 |

OTHER PUBLICATIONS

PCT/AU2018/050879 International Search Report and Written Opinion dated Sep. 10, 2018.
PCT/AU2018/050879 International Preliminary Report on Patentability dated Jul. 15, 2019.
JP 2020-508627 Office Action dated Jul. 19, 2022, English Translation only.
JP 2020-508627 Office Action datedJ an. 24, 2023, English Translation only.
2020-7007871 Office Action dated May 19, 2023, English translation only.

* cited by examiner

MULTI-SPOT OPHTHALMIC LASER

CROSS-REFERENCE TO RELATED APPLICATION

This application is the US national stage of PCT/AU2018/050879 filed Aug. 17, 2018, which claims priority to AU 2017903330 filed Aug. 18, 2017.

FIELD OF THE INVENTION

The present invention relates to the field of laser devices and in particular to an ophthalmic laser device for treatment of eye problems. More particularly, the invention relates to a multi-spot ophthalmic laser.

BACKGROUND TO THE INVENTION

Lasers have been used for many years to treat retinal disorders, predominately using their ability to coagulate tissue. The degree of laser energy absorption in retinal layers and structures is highly dependent on the wavelength used and the effectiveness of controlling the focal point and the energy profile of the laser beam.

In our earlier filed Australian patent application number 2008255642 we describe an ophthalmic laser device useful for improving the function of the retina of the human eye. In the background section of the application we explain the need for effective retinal treatments and describe a laser treatment device that produces a uniform treatment effect. The content of AU2008255642 is incorporated herein by reference in its entirety.

Although the laser treatment device described in AU2008255642 has proven effective, it has been realised that there is still room for improvement. As explained in our earlier patent, the eye deteriorates as a natural result of the aging process. Lasers can be used to rejuvenate the eye and reverse some of the age-related degenerative effects. In particular, cells of the retinal pigmented epithelium (RPE) will regenerate if destroyed by targeted laser treatment. However, in order to be effective the RPE cells need to be targeted with an appropriate energy while neighbouring cells are not exposed to laser energy, or at least are exposed to laser energy at such a low level that there is no discernible effect. Exposing too large a cluster of cells to laser treatment acts against the regeneration process as the cells towards the centre of the cluster do not regenerate. Similarly, too much laser energy produces a thermal shock wave that is detrimental to the regeneration process.

A more precise delivery of energy per cell is required than is currently possible with the device described in AU2008255642 or other prior art devices.

SUMMARY OF THE INVENTION

In one form, although it need not be the only or indeed the broadest form, the invention resides in a multi-spot ophthalmic laser device comprising:
a laser module producing a laser pulse or sequence of laser pulses each having:
  a pulse duration in the range of 10 ps to 20 µs;
  a wavelength in the range 500 nm to 900 nm;
  a pulse energy in the range 10 µJ to 10 mJ per pulse; and
an optical beam profiling module that modifies an output beam profile of each pulse of the laser module to deliver multiple spatially distributed laser spots of defined size and energy;
wherein the spatial distribution of the laser spots is defined by a spot diameter to space ratio in the range 1:2 to 1:20.

Suitably, the optical beam profiling module comprises a multimode optical fibre that modifies the output beam profile of the laser module to produce a substantially uniform beam profile and an optical fibre bundle coupled to the output of the multimode optical fibre that delivers multiple laser spots of defined size, spacing and energy.

The multi-spot ophthalmic laser suitably includes fibre coupling optics that couple an output of the laser module into the multimode optical fibre. The multi-spot ophthalmic laser suitably also includes fibre coupling optics that couples an output of the multimode optical fibre to an input of the optical fibre bundle.

Alternatively, the optical beam profiling module comprises a diffractive optical element and lens in the optical path of the laser output that modifies the beam optically to produce high energy intensity spots.

In a further alternative the optical beam profiling module comprises a mask that blocks parts of the output beam profile only allowing transmission of selected areas of the laser beam and a focusing lens that images the output of the laser module after the mask to form high intensity spots.

In a still further alternative the optical beam profiling module comprises a micro-lens array and focusing lens that images the output of the laser module to form high intensity spots.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
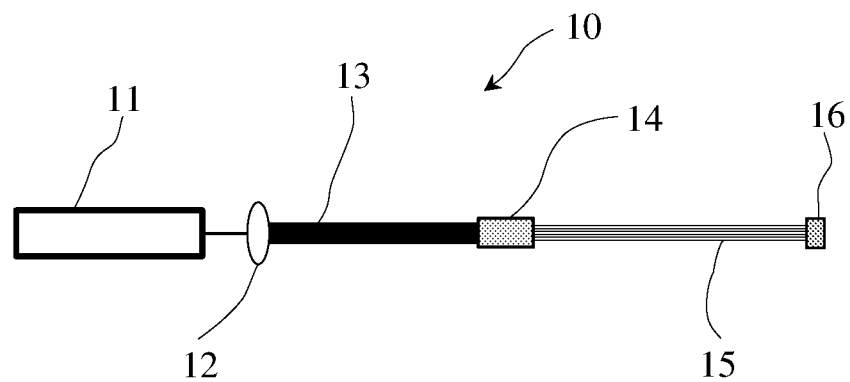
FIG. 1 shows a first embodiment of a multi-spot ophthalmic laser device.

Embodiments of the present invention reside primarily in a multi-spot ophthalmic laser device. Accordingly, the integers of the device have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

Referring to FIG. 1 there is shown a first embodiment of the invention comprising a multi-spot ophthalmic laser device 10 consisting of a laser module 11, optics 12, multimode fibre 13, coupler 14, multi-fibre bundle 15 and output head 16.

The laser module may be any suitable laser that generates the appropriate output. The preferred embodiment of the laser module 11 is frequency doubled, Q-switched flashlamp-pumped Nd:YAG laser producing 532 nm laser pulses. The laser cavity is suitably of conventional design having a 100% reflecting end mirror and a partial reflecting output coupler. The laser rod is excited by a flashlamp that is energized by a high voltage power supply. A passive Q-switch allows the cavity energy to be delivered as very short, high energy pulses. An alternate source of excitation is a semiconductor laser that is used to pump the laser rod.

Although a flashlamp pumped Nd:YAG laser is the preferred embodiment for the laser cavity the invention is not limited to this particular cavity design. Any laser cavity capable of producing pulses in the 20 ps to 20 µs range with a wavelength between about 500 nm and about 900 nm and pulse energy of around 10 µJ to 10 mJ will be suitable. This includes other solid stated materials such as Er:YAG, Nd:YLF, Er:YLF and diode-pumped solid-state laser (DPSSL). Other elements may also be varied. For instance, an active Q-switch may be used instead of a passive Q-switch.

The optics 12 may be a conventional fibre input coupler and may be a lens having an appropriate focal length within the numerical aperture of the multimode fibre 13. The multimode fibre 13 is appropriately a glass fibre with a core diameter of around 400 µm, although this is not a critical dimension. The output of the multimode fibre 13 is coupled to the multi-fibre bundle 15 with a fibre adaptor 14 where both fibre surfaces are kept aligned and in close proximity in such a way that light passing through is not scattered or reflected back by the join. An alternative coupling is to fuse the two fibres, known as fusion splicing which removes the air gap entirely minimising scattering and reflections. The multi-fibre bundle 15 consists of many (up to 500) microfibres grouped and bonded together to make a bundle with a cross-section about the same size as the multimode fibre output, notionally 400 µm. Each micro-fibre is covered by a cladding that reflects the energy back into individual microfibres. The cladding thickness also determines the ratio between the core diameter and the core spacing which is typically 1:4. This may vary dependent on treatment. The result produces a consistent energy within each micro fibre thus delivering a consistent projected energy. The output head 16 permits coupling to suitable delivery optics, such as described in our earlier patent.

Figure 2:
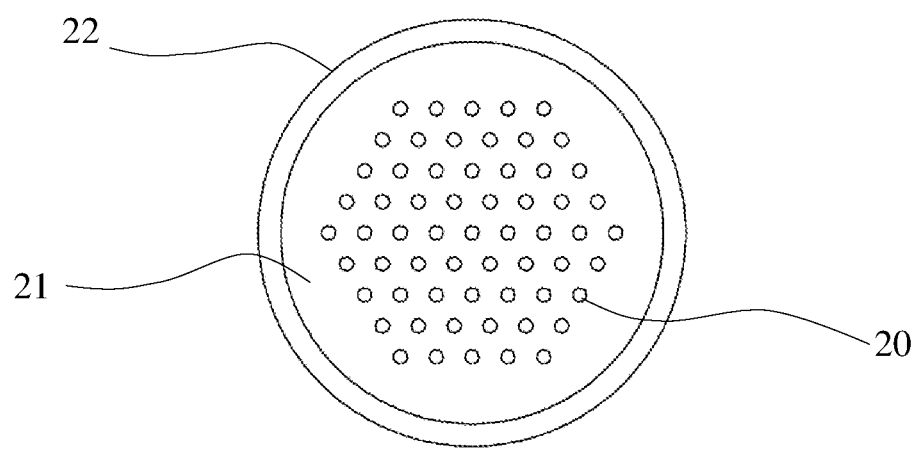
FIG. 2 is an enlarged view of the output tip of the multi-spot ophthalmic laser device of FIG. 1.

An end view of the optical head 16 is shown in FIG. 2. In the embodiment of FIG. 2 the multi-fibre bundle 15 contains 61 micro-core optical fibres 20 in a hexagonal close packing bundle. A cladding 21 surrounds the individual fibres and a polymer coating 22 of around 80 µm thickness surrounds the bundle 15. Each micro-core fibre may have a diameter of 1-50 µm, with 10 µm being particularly suitable as discussed below. The spacing between fibre centres may be in the range 2-200 µm with the preferred spacing being related to the size of the micro-core fibres, the size of the multimode fibre and the treatment regime.

The micro-core fibres may have a diameter of 1 µm, 2 µm, 3 µm, 4 µm, 5 µm, 10 µm, 15 µm, 20 µm, 25 µm, 30 µm, 35 µm, 40 µm, 45 µm, 50 µm or any intermediate size. The spacing between fibre centres may be 2 µm, 3, µm, 4 µm, 5 µm, 10 µm, 20 µm, 30 µm, 40 µm, 50 µm, 75 µm, 100 µm, 125 µm, 150 µm, 175 µm, 200 µm or any intermediate distance.

For instance, in the macular region of the adult eye the cells vary in size due to position and age. Towards the center, the cells are typically 10 µm, whereas toward the periphery they become significantly flatter and wider, and may be as large as 60 µm. The cells typically grow as the eye ages.

Figure 3:
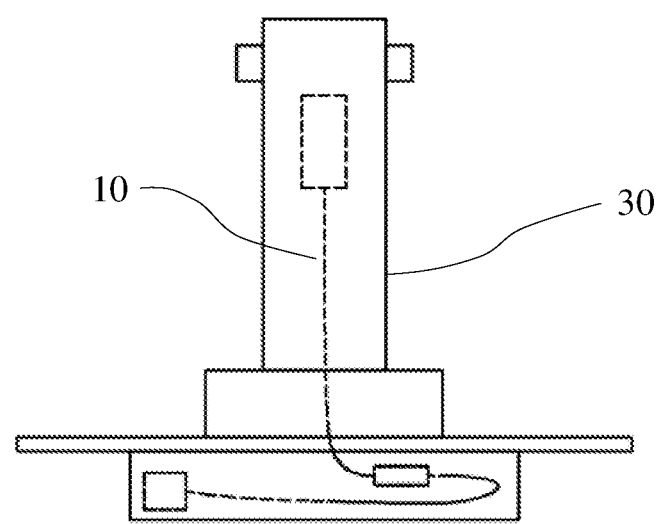
FIG. 3 shows the multi-spot ophthalmic laser device of FIG. 1 embodied in a conventional slit lamp assembly.

The multi-fibre ophthalmic laser device 10 will most often be used with a slit lamp assembly 30 as depicted in FIG. 3. The laser module 11 may be in the base of the slit lamp assembly or nearby. The multimode fibre and multi-fibre bundle are conveniently located within an arm of the slit lamp assembly. The optical head 16 is coupled to other optics in the slit lamp assembly for delivery of laser radiation to the retina.

The delivery optics of the optical head 16 image the output of the micro-core fibre onto a target area. The inventors have determined that a suitable spatial distribution of laser spots is defined by a spot diameter to space ratio. The fibre bundle described above delivers a spot diameter to space ratio in the range 1:2 to 1:20, which has been found to be suitable for ophthalmic treatments. The Inventors have found that a ratio of 1:4 is particularly suitable for maintaining at least two healthy cells between treated cells for cell regeneration.

Figure 4:
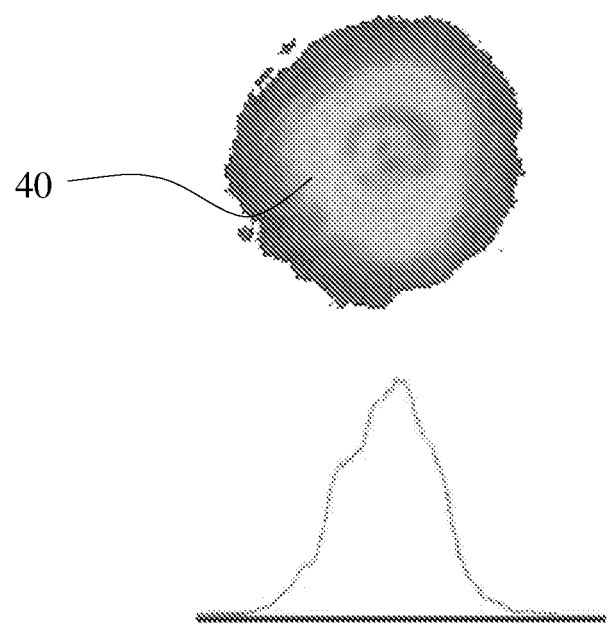
FIG. 4 shows the laser module output for comparison.
Figure 5:
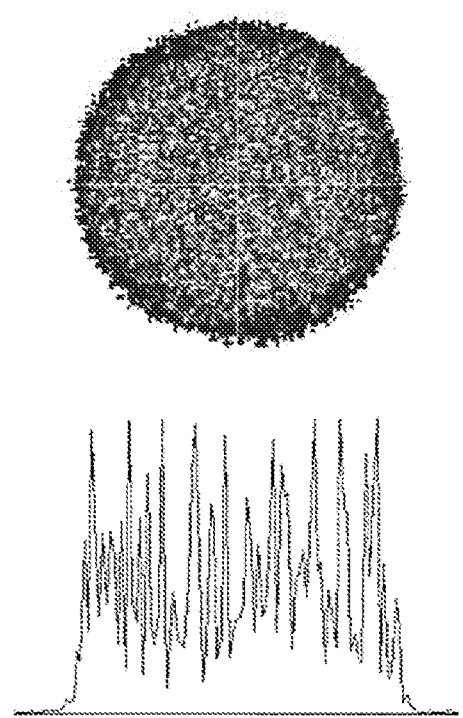
FIG. 5 shows the optical fibre bundle output for comparison.
Figure 6:
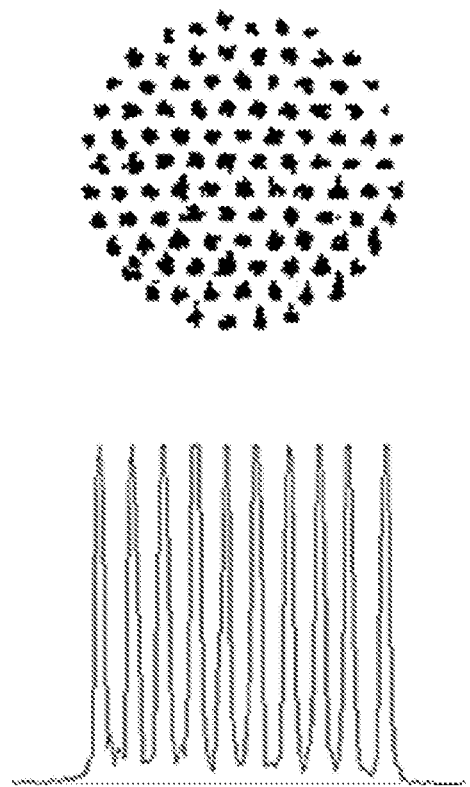
FIG. 6 displays the multi-spot energy profile and spot size.

FIG. 4 shows a typical output from the laser module 11. The output is a typical Gaussian beam profile with a non-uniform energy distribution. This is evident in the hot spot 40. After passing through the multimode fibre 13 the profile demonstrates the speckle pattern shown in FIG. 5. As can be clearly seen, the energy profile is more uniform and the hot spot has been eliminated. This output is coupled to the multi-fibre bundle 15 to deliver the final output shown in FIG. 6.

The multi-fibre ophthalmic laser device delivers consistent energy to each target cell cluster in the retina as well as minimising any energy delivered in between targeted cell clusters. The ratio of energy delivered between targeted and non-targeted area is key to the success of treating age-related diseases.

Five fibres have been built to understand the optimal spacing and the optimal diameter of the micro-fibre. The ideal configuration should ensure all neighbouring RPE cells around an individual treated cell remain intact and free of energy absorption. These fibres have been tested on porcine explants. The results for each configuration outlined below are shown in the respective figure.

Figure 7:
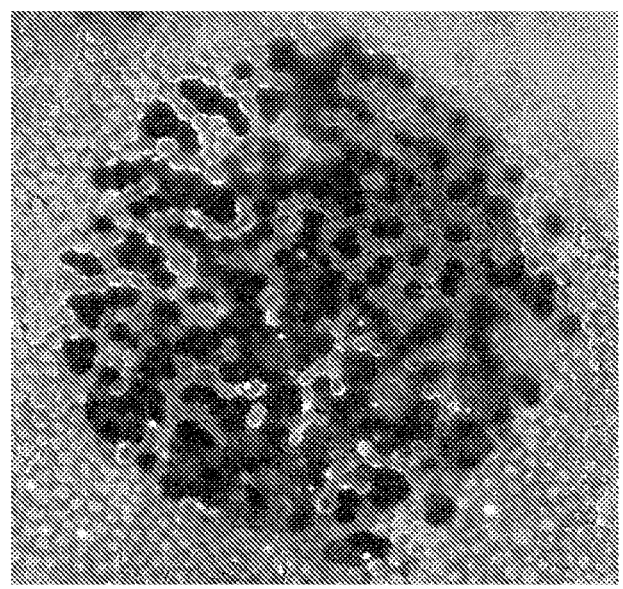
FIG. 7 shows the application of one embodiment of the invention using 10 µm fibres.
Figure 8:
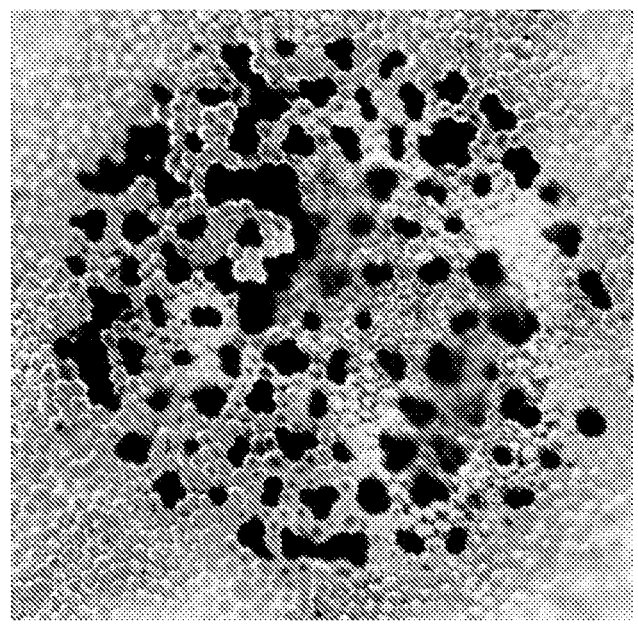
FIG. 8 shows the application of one embodiment of the invention using 7.5 µm fibres.
Figure 9:
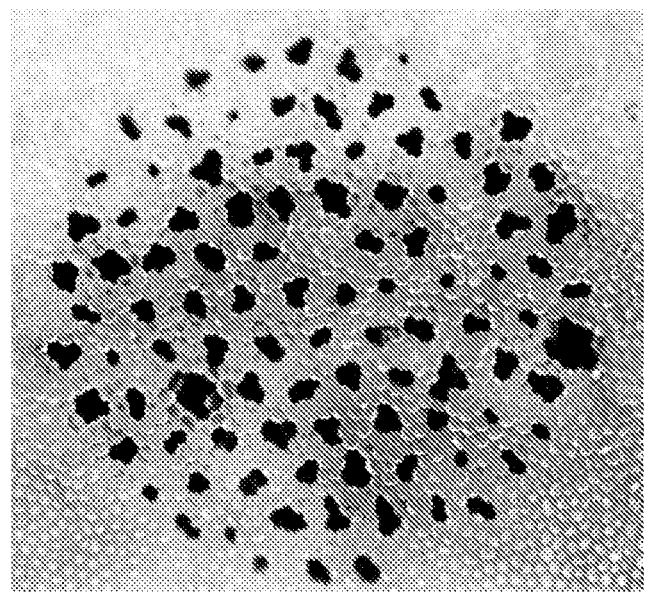
FIG. 9 shows the application of one embodiment of the invention using 5 µm fibres.

| Fibre Size | Fibre Spacing | Output |
| --- | --- | --- |
| 5 µm | 32.5 µm | FIG. 9 |
| 7.5 µm | 32.5 µm | FIG. 8 |
| 10 µm | 32.5 µm | FIG. 7 |
| 15 um | 48.75 um | |
| 20 um | 65 um | |

It is evident from the example output that 5 µm fibres on 32.5 µm spacing provide a result that is able to consistently provide intact neighboring cells throughout the laser spot.

Figure 10:
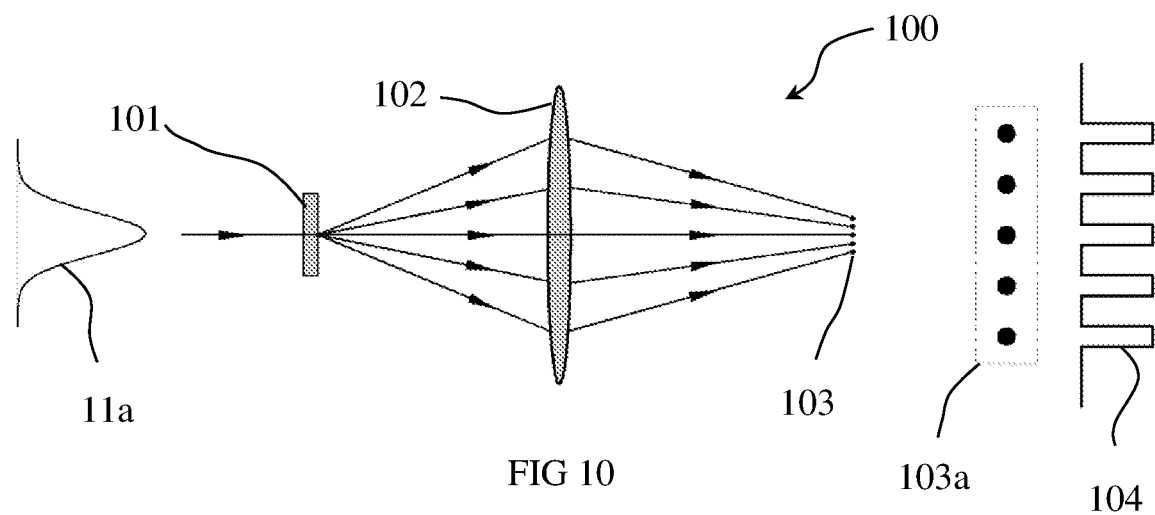
FIG. 10 shows a multi-spot ophthalmic laser device utilising a diffractive optical element.

A second embodiment of the invention is shown in FIG. 10. In this embodiment the optical beam profiling module 100 utilizes a diffractive optical element 101 that modifies the output 11a of the laser module 11 optically to produce multiple spatially distributed laser spots. Looking at FIG. 10 in detail, the laser module output 11a is modified by the diffractive optical element 101 and then focused by a focusing lens 102 to a target 103. The energy peaks at the target 103 have the profile displayed in the enlargement 103a of the target 103 and the graph 104. The diffractive optical element 101 is selected to achieve the energy intensity profile of graph 104 with a spot diameter to space ratio in the range 1:2 to 1:20.

Three diffractive optical elements 101 have been built to understand the optimal spacing and the optimal spot for the element. The ideal configuration should ensure all neighbouring RPE cells around an individual treated cell remain intact and free of energy absorption. These diffractive optical elements have been tested on porcine explants and burn paper. The results for each configuration are outlined below. The 5×5 element is shown in the respective figure.

Figure 13:
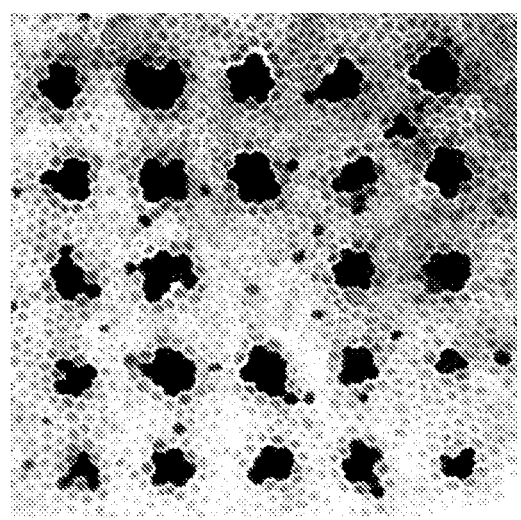
FIG. 13 shows the application of the embodiment of FIG. 10.

| Element Array | Spot Size | Spot Spacing | Output |
| --- | --- | --- | --- |
| 5 × 5 | 10 µm | 100 µm | FIG. 13 |
| 6 × 6 | 10 µm | 80 µm | |
| 9 × 9 | 10 µm | 50 µm | |

Figure 11:
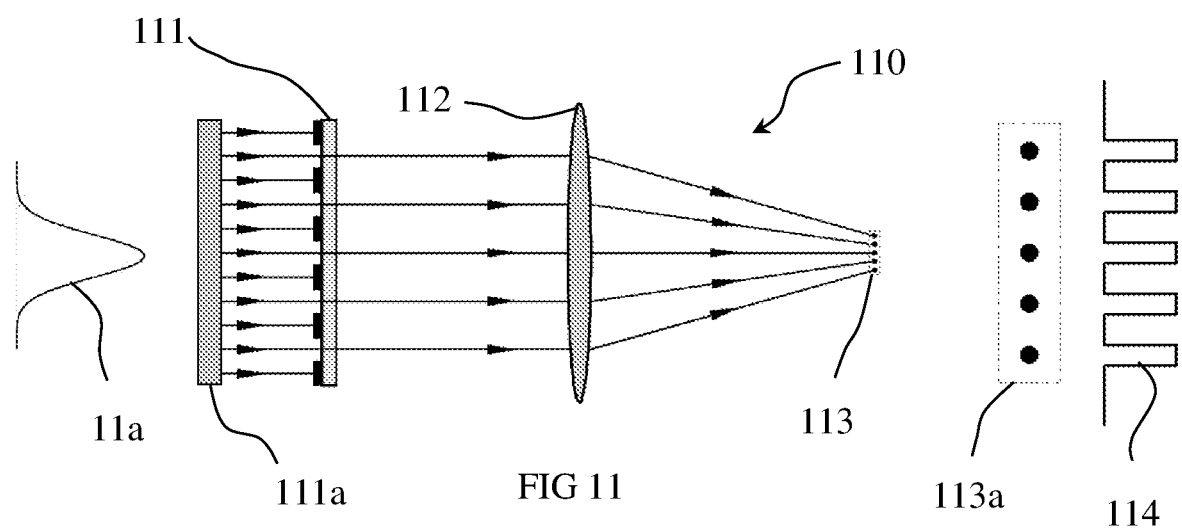
FIG. 11 shows a multi-spot ophthalmic laser device utilising a mask.

A third embodiment of the invention is shown in FIG. 11. In this embodiment the optical beam profiling module 110 has a masked coating 111 that blocks the undesired parts of the beam 11a and transmits the desired parts of the laser beam 11a. The optical beam profiling module 110 also includes a beam expander/homogenizer 111a that modifies the profile of the beam 11a to have a top hat profile before the mask 111. Looking at FIG. 11 in detail, the laser module output 11a is selectively blocked by the mask 111 and then focused by focusing lens 112 to a target 113. The energy peaks at the target 113 have the profile displayed in the enlargement 113a of the target 113 and the graph 114. The masked coating 111 can partially absorb or reflect the incident light to achieve the energy intensity profile of graph 114 with a spot diameter to space ratio in the range 1:2 to 1:20. In a variation on this embodiment the mask could be applied directly to the focusing lens.

Figure 12:
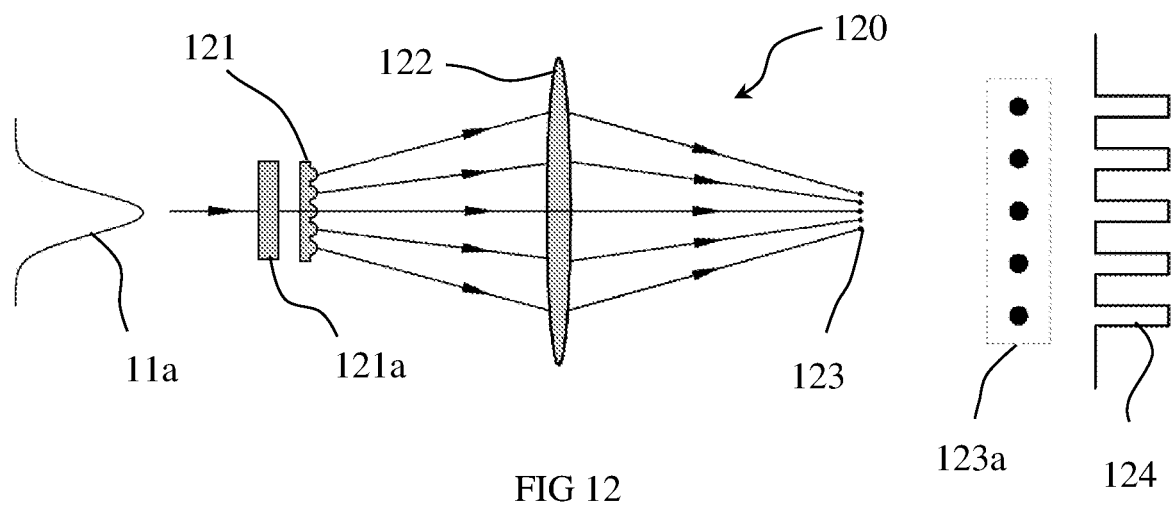
FIG. 12 shows a multi-spot ophthalmic laser device utilising a micro-lens array.

A fourth embodiment of the invention is shown in FIG. 12. In this embodiment the optical beam profiling module 120 has a micro-lens array 121 that is designed to couple together micro beams at the focal plane. The optical beam profiling module 120 also includes a beam homogenizer 121a that modifies the profile of the beam 11a to have a top hat profile before the micro-lens array 121. Looking at FIG. 12 in detail, the laser module output 11a is focused by the micro-lens array 121 into multiple micro beams which are then focused by focusing lens 122 to a target 123. The energy peaks at the target 123 have the profile displayed in the enlargement 123a of the target 123 and the graph 124. The micro lens array 121 is selected to achieve the energy intensity profile of graph 124 with a spot diameter to space ratio in the range 1:2 to 1:20.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that provide the desired output energy profile have been discussed herein, and other embodiments that fall within the spirit and scope of the above described invention.

The invention claimed is:

1. A multi-spot ophthalmic laser device for improving function of a retina of a human eye by laser irradiation through a cornea of the eye to retinal pigmented epithelium comprising:
   a Q-switched laser module producing a laser pulse or sequence of laser pulses each having: a pulse duration in the range of 10 ps to 20 µs;
   a wavelength in the range of 500 nm to 900 nm;
   a pulse energy in the range of 00 to 10 mJ per pulse; and
   an optical beam profiling module that modifies an output beam profile of each pulse of the Q-switched laser module to deliver multiple spatially-distributed laser spots of defined size and energy;
   wherein a spatial distribution of the laser spots is defined by a spot diameter to space ratio in the range 1:2 to 1:20,
   wherein each laser spot has a diameter of from 1 µm to 50 µm,
   wherein spacing between laser spots is in the range of 2 µm to 200 µm,
   wherein the optical beam profiling module comprises a multimode optical fibre that modifies the output beam profile of the Q-switched laser module to produce a uniform beam profile and an optical fibre bundle coupled to the output of the multimode optical fibre to deliver the multiple spatially-distributed laser spots of defined size and energy,
   wherein the multimode optical fibre has a core diameter of about 400 µm,
   wherein the optical fibre bundle comprises optical fibres with a core diameter of 1 µm to 50 µm,
   wherein the optical fibres of the optical fibre bundle comprise up to 500 micro-fibres grouped and bonded together in a hexagonal close packing bundle to make a bundle with a cross-section about the same size as the multimode optical fibre of about 400 µm,
   wherein each respective micro-fibre of the up to 500 micro-fibres is covered by a cladding that reflects energy back into the respective micro-fibre, wherein a thickness of the cladding determines a ratio between the core diameter and core spacing of about 1:4 to produce a consistent projected energy within each respective micro-fibre thus delivering a consistent projected energy, and wherein the multimode optical fibre and the optical fibre bundle are fused together to remove an air gap between the multimode optical fibre and the optical fibre bundle minimizing scattering and reflections.

2. The multi-spot ophthalmic laser device of claim 1 wherein the spatial distribution of the laser spots is defined by the spot diameter to space ratio of 1:4 to 1:8.

3. The multi-spot ophthalmic laser device of claim 2 wherein the spatial distribution of the laser spots is defined by the spot diameter to space ratio of 1:4.

4. The multi-spot ophthalmic laser device of claim 1 wherein the optical fibre bundle comprises optical fibres with a core diameter of 10 μm.

5. The multi-spot ophthalmic laser device of claim 1 wherein the optical beam profiling module comprises a diffractive optical element and a focusing lens.

6. The multi-spot ophthalmic laser device of claim 1 wherein the optical beam profiling module comprises a mask that blocks parts of the output beam profile, only allowing transmission of portions of the output beam, and a focusing lens.

7. The multi-spot ophthalmic laser device of claim 1 wherein the optical beam profiling module comprises a micro-lens array and a focusing lens.

\* \* \* \* \*